United States Patent [19]

Bidwell

[11] 4,249,523
[45] Feb. 10, 1981

[54] ADJUSTABLE ORTHOPEDIC FOOT SPLINT

[75] Inventor: Robert E. Bidwell, Melville, N.Y.

[73] Assignee: BioResearch Inc., Farmingdale, N.Y.

[21] Appl. No.: 36,751

[22] Filed: May 7, 1979

[51] Int. Cl.³ ............................................. A61F 3/00
[52] U.S. Cl. ................................... 128/80 A; 128/88
[58] Field of Search ............... 128/80 A, 80 R, 87 R, 128/88, 583

[56] References Cited

U.S. PATENT DOCUMENTS

| | | | |
|---|---|---|---|
| 2,514,870 | 7/1950 | Israel | 128/80 A |
| 2,906,261 | 9/1959 | Craig | 128/80 A |
| 2,963,020 | 12/1960 | Moran | 128/80 A |
| 3,477,426 | 11/1969 | Wincheski | 128/80 R |
| 4,040,416 | 8/1977 | Zentman | 128/80 A |

Primary Examiner—John D. Yasko
Attorney, Agent, or Firm—Larson, Taylor and Hinds

[57] ABSTRACT

An adjustable orthopedic foot splint is disclosed which maintains a desired angle between the feet of the user but which otherwise allows virtually full freedom of movement of the feet. Movements of the feet which are allowed include: forwards and backwards; up and down; together and apart; and tilting of the toe upwards and downwards. Thus, the user can walk, climb steps, or crawl in an approximately normal manner.

In a preferred embodiment, hinged pairs of parallelogram links pivotally interconnect the shoes of the user. In another preferred embodiment, the pivotal connection is vertically adjustable and is resiliently urged to a horizontal position.

23 Claims, 6 Drawing Figures

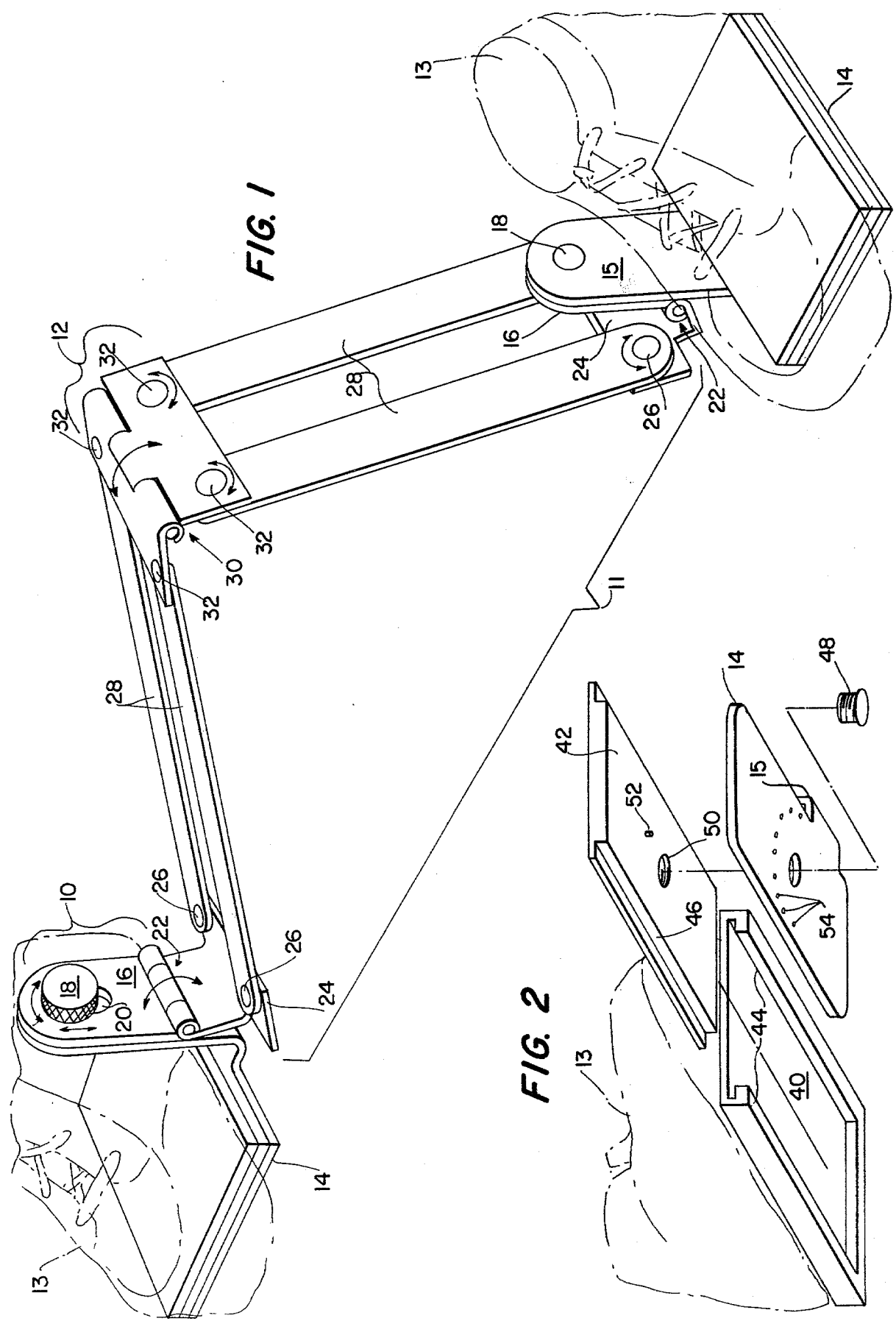

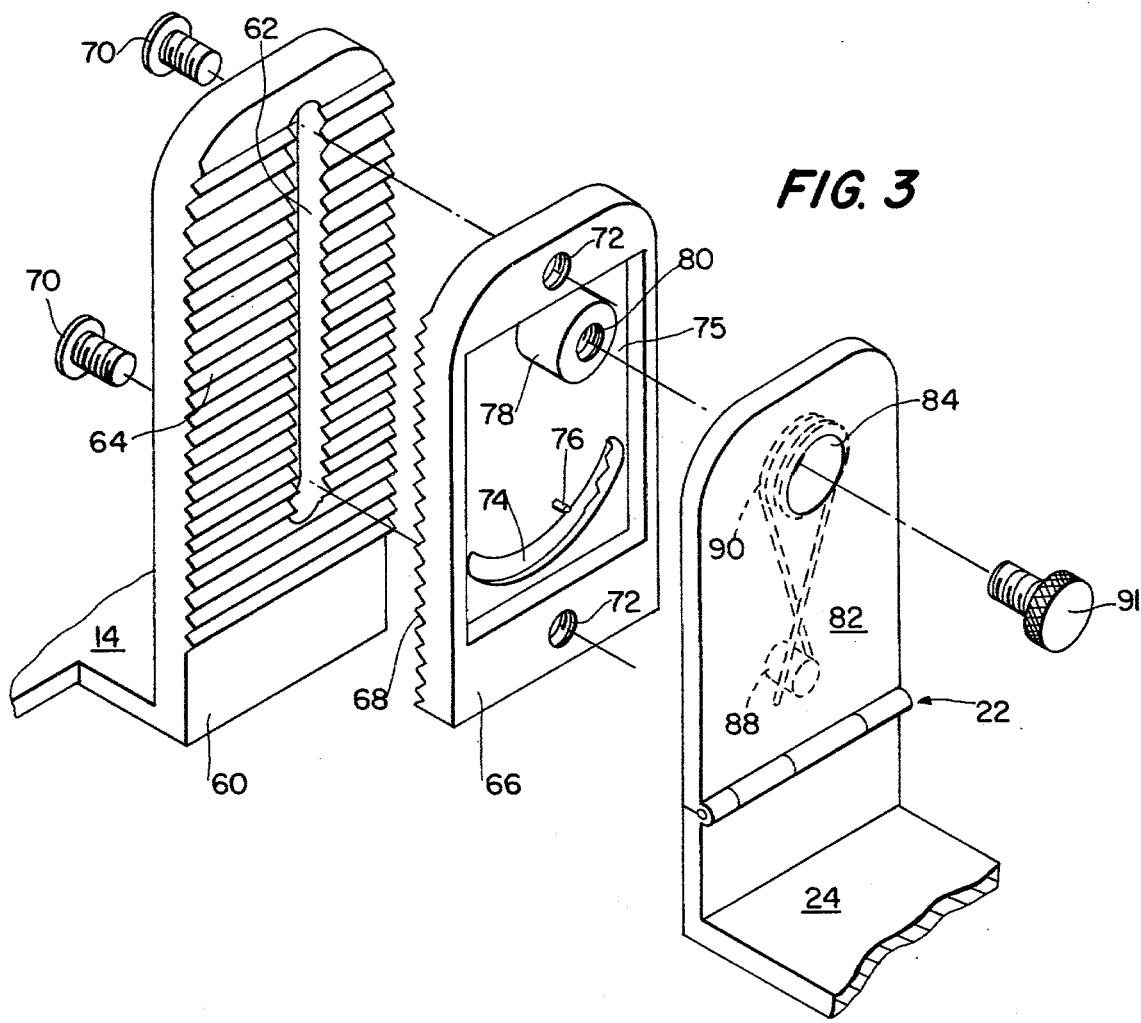
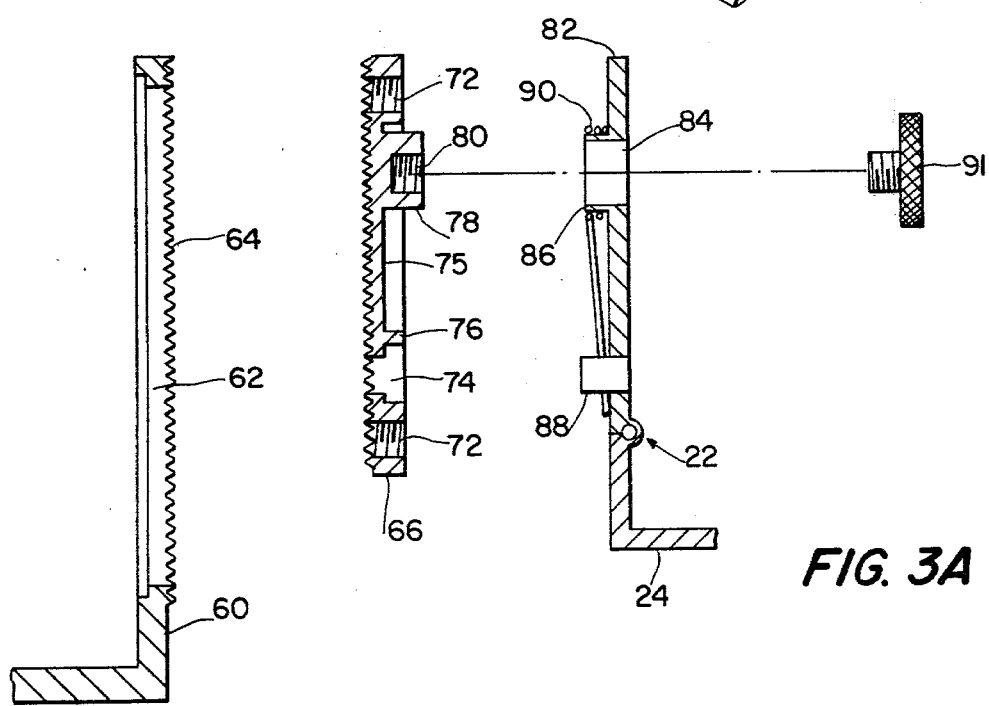
FIG. 3
FIG. 3A

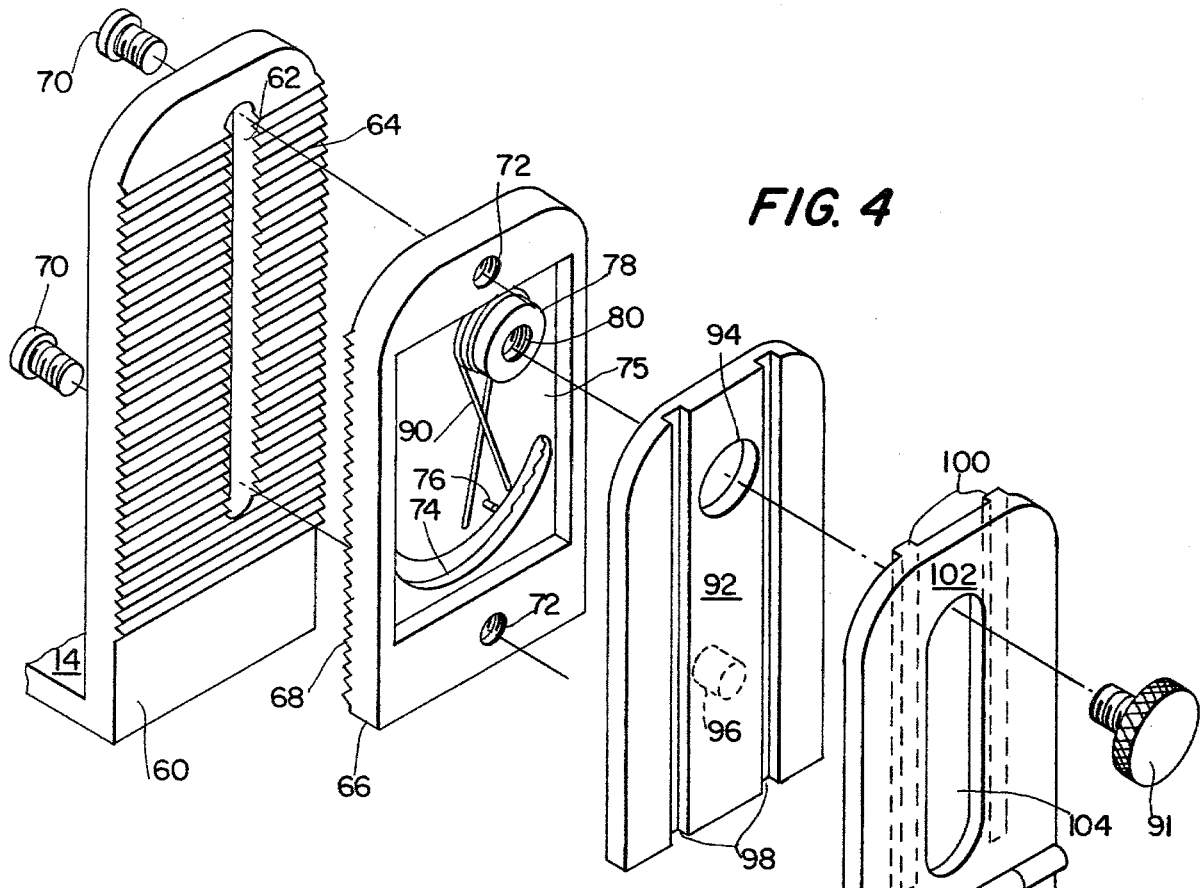
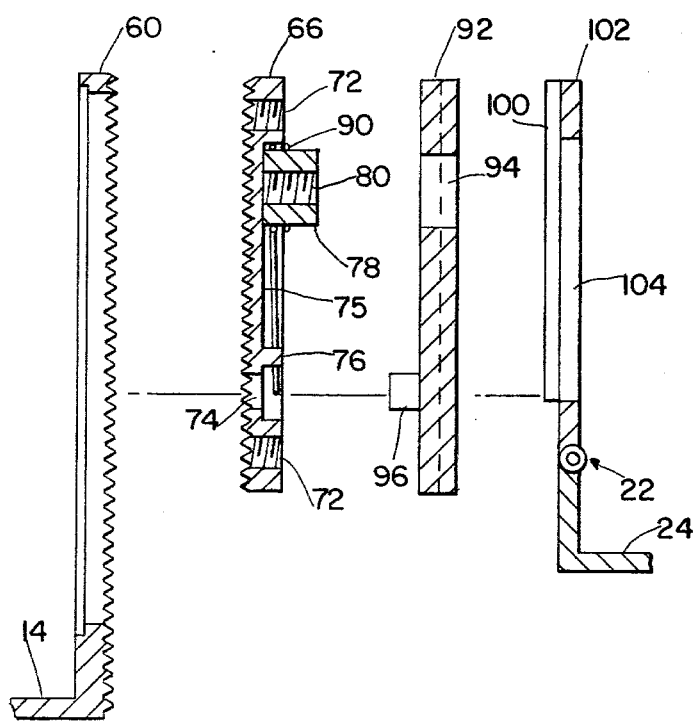
FIG. 4
FIG. 4A

ADJUSTABLE ORTHOPEDIC FOOT SPLINT

FIELD OF THE INVENTION

This invention relates generally to the field of orthopedic splints which maintain a desired angle between the feet, and more particularly, to such a device which allows the feet to move in an otherwise normal manner.

BACKGROUND OF THE INVENTION

In general, an orthopedic splint is useful in correcting bone deformities, particularly in children, by holding the patient's feet at an appropriate corrective angle. Thus, if a patient's feet are abnormally toed-in, it is recommended that the patient wear a splint for a specified period which will hold the feet in a corrective toed-out position. A common type of prior art device, as disclosed in U.S. Pat. Nos. 2,920,620 to Rogers; 4,040,416 to Zentman; and 4,088,129 to DiGiulio, includes a pair of shoes mounted on a flat bar. The shoes in these devices are adjustable on the bar to provide a variety of different toe-in and toe-out angles. Unfortunately, these prior art devices are extremely uncomfortable to the patient as they maintain the feet in almost rigid positions. Even the patent to Zentman which includes a flexible spacer bar to allow a slight amount of vertical movement does little to alleviate this problem. In addition, the patient cannot move except by hopping, which is dangerous and perhaps impossible for young children to perform.

To overcome this almost total lack of mobility and extreme discomfort, prior art devices have been proposed which do allow some movement as well. For instance, in U.S. Pat. No. 2,963,020 to Moran, a device is disclosed which comprises a separate member attached to each shoe of the patient which members are connected by parallelogram links. These linkages are pivotally attached to each shoe member and this allows movement of the feet both upwards and downwards, and forwards and rearwards. In addition, the length of the linkages is manually adjustable. U.S. Pat. No. 3,487,829 to Barnett also discloses parallelogram links connecting shoe engaging members. In this device, the parallelogram links are attached to the shoe engaging members by ball and socket joints. This device also allows the feet to move forwards and backwards, and upwards and downwards, as well as allowing the toes of the feet to tilt upwards or downwards somewhat.

However, none of the foregoing prior art devices has a readily adjustable foot splint which provides for virtually full freedom of movement while still maintaining a desired angle between the feet. In particular, none of the foregoing devices could be easily used by a small child just learning to walk. While the devices disclosed in the patents to Moran and Barnett allow some freedom of movement, these devices are still uncomfortable because they maintain the feet a definite distance apart. This would be especially uncomfortable for a sleeping patient who wished to roll over. It also makes it difficult to stand up, especially for a small child.

SUMMARY OF THE INVENTION

The present invention provides a novel apparatus for holding a patient's feet at a desired angle. The present invention also provides a means for selecting a variety of different angles at which the patient's feet can be maintained.

An object of the invention is to provide a device which maintains a patient's feet at a desired angle while still providing the feet with almost full mobility otherwise. Thus, the patient can walk, climb stairs, or crawl in an approximately normal manner.

It is a further object of the invention to provide for a more comfortable apparatus for holding the feet at a desired angle. With the exception of the angle between the patient's feet, this device allows the patient to move his feet to almost any position which he finds comfortable. In addition, the discomfort of not being relatively ambulatory is also eliminated.

It is a feature of the present invention to use a pair of parallelogram links to connect and maintain the patient's feet at a desired angle. In addition, it is a further feature of the present invention to provide various pivot means in the device to allow almost unlimited movement of the feet. Specifically, this invention allows the feet of a patient, which are at all times maintained at a desired angle with respect to each other, to move in the following directions: upwards and downwards, forwards and backwards; together and apart; and tilting upwards and downwards. In a preferred embodiment, these pivot means take the form of hinges and pivot points.

It is a further feature of another embodiment of the present invention to provide adjustable mounts for the parallelogram links. In addition, the tilting of the feet can be restricted and urged towards a parallel relationship.

Other features, objects and advantages of the present invention are stated in or apparent from the detailed description of the presently preferred embodiments of the invention found hereinbelow.

BRIEF DESCRIPTION OF THE DRAWINGS

FIG. 1 is a perspective view of an embodiment of an orthopedic foot splint.

FIG. 2 is an expanded perspective view of the adjustable shoe engaging means used in one embodiment of the present invention.

FIGS. 3 and 3A are an expanded perspective view and a side view, respectively, showing another embodiment of the orthopedic foot splint with a link positioning means and a restrictive tilting mechanism.

FIGS. 4 and 4A are an expanded perspective view and a side view, respectively, showing another embodiment of a link positioning means.

DETAILED DESCRIPTION OF THE PREFERRED EMBODIMENTS

With reference now to the drawings in which like numerals represent like elements throughout the several views, a presently preferred embodiment of the present invention is depicted in FIG. 1 along with shoes 13 which the patient wears when using the orthopedic foot splint. Briefly, the operative portions of the foot splint include a plate pivot means 10, a linkage means 11 and a central pivot means 12.

Each patient using the foot splint wears a special pair of fitted shoes 13, and each shoe 13 is attached to a shoe engaging plate 14 by a suitable means. To provide a pivot means 10, an upstanding plate 15 extends upwards along the inside edge of each shoe engaging plate 14. A pivot arm 16 is attached to each upstanding plate 15 by means of rivets 18. Each rivet 18 is used to form a pivot axis about which pivot arm 16 pivots. Each pivot arm 16 also includes a vertical slot 20 so that each pivot arm has a means to slide vertically in relation to the pivot axis along the face of upstanding plate 15. In this embodiment, the distal end of each pivot arm 16 forms one leaf of a hinge element 22. Each hinge element 22 has a horizontally extending pivot axis. The other leaf of each hinge element 22 has an inwardly directed right angle turn 24.

Linkage means 11 includes two pairs of parallelogram links 28. Each pair of parallelogram links 28 is pivotally connected to a corresponding right angle turn 24 by rivets 26. Finally, central pivot means 12 includes a central hinge element 30 which interconnects each pair of parallelogram links 28 to form a unitary foot splint. Central hinge element 30 has a horizontally extending axis which is parallel to the axis of hinge element 22. Additionally, each pair of parallelogram links 28 are pivotally attached to a respective leaf of central hinge element 30 by rivets 32 so that each pair of parallelogram links 28 remain parallel at all times when the pairs of parallelogram links 28 pivot.

Referring now to FIG. 2, a means to adjustably attach shoe 13 to shoe engaging plate 14 at a plurality of different angular orientations is shown. The means includes a mounting plate 40 which is rigidly attached to the sole of shoe 13. Mounting plate 40 is designed to slide onto an angular adjusting plate 42 by means of inturned edges 44 on mounting plate 40 which mate with reduced edges 46 on angular adjusting plate 42. In turn, angular adjusting plate 42 is designed to be attached to shoe engaging plate 14 by means of a screw 48 which passes through shoe engaging plate 14 to a threaded bore 50 in angular adjusting plate 42. A pin 52, depending from angular adjusting plate 42, is received in one of a plurality of correspondingly spaced receiving holes 54 in shoe engaging plate 14. When screw 48 attaches angular adjusting plate 42 to shoe engaging plate 14, pin 52 prevents angular adjusting plate 42 from rotating on shoe engaging plate 14 about screw 48. The thickness of angular adjusting plate 42 must also be less than the depth from the bottom surface of mounting plate 40 to the bottom surface of inturned edges 44. Thus, as angular plate 42 is pulled down towards shoe engaging plate 14 by screw 48, angular plate 42 acts to hold mounting plate 40 frictionally against shoe engaging plate 14. Therefore, when screw 48 is snug, shoe 13, mounting plate 40, angular adjusting plate 42 and shoe engaging plate 14 are all rigidly held together as a unit.

In operation, the foot splint is used in the following manner. After determining the angle at which the patient needs his feet to be kept, screw 48 is loosened enough to permit angular adjusting plate 42 to rotate about screw 48. Pin 52 is then moved to a receiving hole 54 which corresponds to the angle at which the feet are to be kept. Next, screw 48 is tightened and the patient puts on shoes 13. The foot splint acts to keep shoes 13 always at the angular orientation which was chosen. However, shoes 13 remain free to move in an otherwise almost normal manner. By way of illustration, the patient's feet can move forward and backwards as parallelogram links 28 pivot on rivets 26 and 32. The patient's feet also move upwards and downwards by reason of hinge elements 22 and central hinge 30. Hinge elements 22 and central hinge 30 also allow the patient's feet to move together and apart. Lastly, the patient's feet can tilt upwards and downwards as well due to the action of plate pivot means 10. Thus the patient can walk or climb steps in an almost normal manner. And if the foot splint is used on an infant, not only can the infant crawl in an almost normal manner, but the infant's efforts towards learning to walk is not unduly impeded. The only movement which is impeded is the toeing-in or toeing-out of the feet.

With reference now to FIGS. 3 and 3A, an alternative embodiment of plate pivot means 10 is depicted. In this embodiment, means are provided to raise and lower the pivot axis of pivot arm 82. A means is also provided to limit the angular pivoting of pivot arm 82 and to urge pivot arm 82 to a position perpendicular to shoe engaging plate 14. Only a portion of shoe engaging plate 14 is shown, and this portion shows upstanding plate 60 attached along the inside edge of shoe engaging plate 14. Also depicted are facing plate 66 and pivot arm 82 which includes hinge element 22. Upstanding plate 60 has a vertical slot 62 therethrough, and the inner face is covered with a series of horizontal grooves forming a serrated face 64. Located opposite serrated face 64 is a matching serrated face 68 on facing plate 66. Facing plate 66 is attached to upstanding plate 60 by screws 70 which pass through vertical slot 62 and engage facing plate 66 in threaded bore 72. Facing plate 66 also has an arcuate keyway 74 therethrough. Located in a recessed portion 75 on the face of facing plate 66 opposite to serrated face 68 are a peg 76 and a pivot post 78 having a threaded bore 80. Pivot post 78 extends beyond the face of facing plate 66, a distance which is slightly longer than the thickness of upstanding plate 82. Pivot arm 82 has a bore 84 which pivot post 78 extends through slightly. In addition, a pivot sleeve 86 extends outward from the face of pivot arm 82 and extends around pivot post 78. A raised key 88 also extends outward from the face of pivot arm 82. Surrounding pivot sleeve 86 is a spiral spring 90 whose ends are crossed and lie on either side of raised key 88. A screw 91, which passes through bore 84 into threaded bore 80, attaches pivot arm 82 to facing plate 66.

In operation, this alternative embodiment of plate pivot means 10 functions in the following manner. Depending on what is most comfortable or preferred by the patient, the position of right angle turn 24 and hence the height of linkage means 11 relative to shoe engaging plate 14, which is the walking surface, can be adjusted. This adjustment is accomplished by attaching facing plate 66 to upstanding plate 60 at a variety of different heights which causes the pivot axis of pivot arm 60 and right angle turn 24 to move as well. To adjust the height of facing plate 66, screws 70 are loosened until there is sufficient clearance between serrated faces 64 and 68 to allow facing plate 66 to slide along upstanding plate 60. It is then a simple matter to select the height of facing plate 66 which the patient prefers and to tighten screws 70. The engagement of matching serrated faces 64 and 68 locks facing plate 66 onto upstanding plate 60 as screws 70 are tightened. Linkage means 11, whose height is determined by facing plate 66, is likewise positioned at the selected height.

The means to limit the angular pivoting of pivot arm 60 and to urge pivot arm 60 to a position perpendicular to shoe engaging plate 14 function in the following manner. Screw 91 is used to attach pivot arm 82 to facing plate 66. Screw 91 is not tightened until key 88 extends into arcuate keyway 74 and peg 76 is located between the two crossed ends of spiral spring 90. When screw 91 is tightened down, it engages the end of pivot post 78 so that pivot arm 82 pivots freely about pivot post 78. However, with key 88 in arcuate keyway 74, the pivoting of pivot arm 82 is restricted by the travel of key 88 from one end of arcuate keyway 74 to the other. In addition, as pivot arm 82 moves away from a perpendicular orientation peg 76 engages a corresponding end of spiral spring 90 while the other end of spiral spring 90 engages key 88. This causes spiral spring 90 to exert a force on pivot arm 82, urging it back to a perpendicular orientation where neither end of spiral spring 90 is engaged with peg 76.

Another embodiment of plate pivot means 10, which additionally provides a means to allow hinge element 22 to slide vertically with respect to upstanding plate 60, is depicted in FIGS. 4 and 4a. Like the previous embodiment of plate pivot means 10, this embodiment includes an upstanding plate 60 and a facing plate 66 which are relatively adjustable as previously described. Mounted on pivot post 78 of facing plate 66 is spiral spring 90 whose crossed ends lie on either side of peg 76. Also mounted rotatably on pivot post 78 by a bore 94 is a pivot arm 92. Pivot arm 92 includes a raised key 96 on one face which extends into arcuate keyway 74 in facing plate 66. On the other face of pivot arm 92, two vertical channels 98 are positioned on either side of bore 94. Two mating raised ridges 100 on a sliding plate 102 ride in vertical channels 98. Sliding plate 102 includes a vertical slot 104 through which the end of pivot post 78 protrudes slightly. Hinge element 22 is attached at the lower end of sliding plate 102. A screw 90, passing through bore 94 and vertical slot 104 into threaded bore 80 of pivot post 78, holds pivot arm 92 and sliding plate 102 on facing plate 66.

In operation, this embodiment functions much like the embodiment discussed previously. Facing plate 66 is vertically adjustable relative to upstanding plate 60 and the angular pivoting of pivot arm 92 is both restricted and urged perpendicular. Unlike the previous embodiment, however, hinge element 22 can slide vertically with respect to pivot arm 92 and hence upstanding plate 60. When a vertical force is exerted on hinge element 22, sliding plate 102 moves freely along pivot arm 92 guided by raised ridges 100 sliding in vertical channels 98. The vertical movement of sliding plate 102 is limited by the ends of vertical slot 104 in which pivot post 78 extends.

Although the invention has been described with respect to exemplary embodiments thereof, it will be understood by those of ordinary skill in the art that variations and modifications may be effected within the scope and spirit of the invention. Thus, for example, central pivot means 12 would employ a ball and socket joint instead of the hinge and pivoting means for the links described. Similarly, the hinge and pivoting means for the links at the pivot arm could also be replaced with a universal type joint. Other variations and modifications of the present invention are also possible.

I claim:
1. An orthopedic foot splint comprising:
a pair of shoe engaging plates;
linkage means interconnecting said pair of shoe engaging plates;
horizontally extending plate pivot means interconnecting each end of said linkage means with one of said pair of shoe engaging plates;
said linkage means including two pairs of parallelogram links having a central horizontally extending interconnecting pivot means;
whereby each of said shoe engaging plates are prevented from any relative rotation about a vertical axis with respect to each other so that the shoes of a patient are fixed in a selected angular relationship to each other, but permitting freedom of movement of shoes of a patient about axes other than the vertical axis.

2. An orthopedic foot splint as claimed in claim 1 wherein
said horizontally extending plate pivot means includes a hinge element with a horizontally extending axis and a pivot arm which pivots about a horizontal axis perpendicular to the horizontal axis of said hinge element.

3. An orthopedic foot splint as claimed in claim 2 wherein
said central pivot means includes a central hinge element having an axis parallel to the longitudinal axis of said hinge element, each leaf of said central hinge element being pivotally connected to one of said pairs of parallelogram links.

4. An orthopedic foot splint as claimed in claim 1 further including
means to adjustably attach the shoes of the patient to said shoe engaging plates at a plurality of different angular orientations.

5. An orthopedic foot splint comprising:
a pair of shoes engaging plates for engagement with the shoes of a patient,
means interconnecting said pair of shoe engaging plates, said interconnecting means comprising
a pair of plate pivot means, each of said plate pivot means being pivotally attached at one end thereof, to one of said shoe engaging plates,
a central hinge element, and
a pair of parallelogram links pivotally interconnected on each side of said central hinge with a plate pivot means,
whereby each of said shoe engaging plates are prevented from any relative rotation about a vertical axis with respect to each other so that the shoes of a patient are fixed in a selected angular relationship to each other, but permitting freedom of movement of shoes of a patient about axes other than the vertical axis.

6. An orthopedic foot splint as claimed in Claim 5 wherein
said pivot plate means includes a hinge element with a horizontally extending axis which is pivotally connected to one of said pair of parallelogram links at one end, and a pivot arm which pivots about a horizontal axis perpendicular to the horizontal axis of said hinge element and which is attached at the pivot point to one of said shoe engaging plates and attached on the arm to said hinge element.

7. An orthopedic foot splint as claimed in claim 6 further including
means to adjustably attach the shoes of the patient to said plates at a plurality of different angular orientations such that the angles between the shoes are adjustable.

8. An orthopedic foot splint as claimed in claim 7 further including
vertical sliding means which allow said pivot arm to be vertically slidable on the pivotal axis of pivot arm such that said pivot arm may be moved in a vertical direction while remaining pivotable at all times.

9. An orthopedic foot splint as claimed in claim 7 further including means to adjustably raise and lower the pivot point of said pivot arm such that said parallelogram links are adjustable to a plurality of different vertical positions.

10. An orthopedic foot splint as claimed in claim 9 further including
means to limit the angular pivoting of said pivot arm.

11. An orthopedic foot splint comprising:
splint means for each shoe of the patient, each of said splint means comprising,
a shoe engaging plate
a hinge element having a horizontal pivot disposed substantially parallel to the longitudinal axis of the shoe,
plate pivot means interconnecting said hinge element with said shoe engaging plate, the horizontal axis of said plate pivot means extending substantially normal with respect to the longitudinal axis of the shoe,
a pair of parallelogram links pivoted to said hinge element, and
a central hinge, interconnecting said pair of parallelogram links extending from each shoe engaging plate, the pivot of said central hinge extending parallel to the pivot of said hinge elements,
whereby each of said shoe engaging plates are prevented from any relative rotation about a vertical axis with respect to each other so that the shoes of a patient are fixed in a selected angular relationship to each other but permitting freedom of movement of shoes of a patient about axes other than the vertical axis.

12. An orthopedic foot splint as claimed in claim 11 wherein
said central hinge is pivotally connected on each side to one of said pairs of parallelogram links.

13. An orthopedic foot splint as claimed in claim 12 further including
means to adjustably attach each shoe of the patient to said shoe engaging plate at a plurality of different angular orientations.

14. An orthopedic foot splint as claimed in claim 13 further including
means to adjustably raise and lower the pivot point of said plate pivot means including
an upstanding plate attached to the inner side of said shoe engaging plate, and
a facing plate which is adjustably attached to said upstanding plate; and
a pivot arm which is attached at the pivot point to said facing plate.

15. An orthopedic foot splint as claimed in claim 14 further comprising
an inwardly directed right angle turn on the leaf of said hinge element which is attached to said parallelogram links, and to which said parallelogram links are pivotally attached.

16. An orthopedic foot splint as claimed in claim 15 wherein
said upstanding plate and said facing plate have matching serrated faces such that relative movement of the two is more easily prevented.

17. An orthopedic foot splint as claimed in claim 14 wherein
said means to attach each of the shoes to said shoe engaging plate at a plurality of different angular orientations includes
an angle adjusting plate, and
a mounting plate, attached to the sole of each shoe, which is aligned with said angle adjusting plate;
such that each of the shoes is adjustably attached to said shoe engaging plate and the position of said angle adjusting plate determines the anlge between the shoes.

18. An orthopedic foot splint as claimed in claim 17 wherein
said means to adjustably attach each shoe to said shoe engaging plate at a plurality of different angular orientations further includes:
a pin extending downward from said angle adjusting plate; and
a plurality of receiving holes located in said shoe engaging plate;
such that the angular orientation of each shoe is adjusted as said pin is moved from one receiving hole to another.

19. An orthopedic foot splint as claimed in claim 14 further including
means to limit the angular pivoting of said pivot arm, relative to said facing plate.

20. An orthopedic foot splint as claimed in claim 19 further including
a raised key rigidly attached to said pivot arm; and
an arcuate keyway in said facing plate;
such that said raised key travels in said keyway and the angular pivoting of said pivot arm is limited by the travel of said raised key in said arcuate keyway.

21. An orthopedic foot splint as claimed in claim 19 further including
means to resiliently urge said pivot arm to remain in a position in which the longituindal axis of said pivot arm is perpendicular to the plane of said shoe engaging plate.

22. An orthopedic foot splint as claimed in claim 21 further including
means to allow said hinge element to slide vertically with respect to said pivot means.

23. An orthopedic foot splint as claimed in claim 22 further comprising
at least one vertically extending channel in said pivot arm; and
at least one raised ridge, corresponding to said vertically extending channel, on one leaf of said hinge element;
such that said raised ridge slides in said channel as said hinge element slides vertically with respect to said pivot arm.

* * * * *